United States Patent [19]
Lord et al.

[11] Patent Number: 5,328,460
[45] Date of Patent: Jul. 12, 1994

[54] IMPLANTABLE MEDICATION INFUSION PUMP INCLUDING SELF-CONTAINED ACOUSTIC FAULT DETECTION APPARATUS

[75] Inventors: Peter C. Lord, Valencia; John R. Schultz, Burbank; David G. Powell, South Pasadena, all of Calif.

[73] Assignee: Pacesetter Infusion, Ltd., Sylmar, Calif.

[21] Appl. No.: 77,889

[22] Filed: Jun. 11, 1993

Related U.S. Application Data

[63] Continuation of Ser. No. 718,709, Jun. 21, 1991, abandoned.

[51] Int. Cl.$^5$ .............................................. A61M 5/20
[52] U.S. Cl. .............................. 604/67; 128/DIG. 12; 128/DIG. 13
[58] Field of Search ................. 73/587, 593, 646; 128/DIG. 12, DIG. 13; 604/67, 56, 118, 141, 891.1, 891.2

[56] References Cited

U.S. PATENT DOCUMENTS

| | | | |
|---|---|---|---|
| 3,731,681 | 5/1973 | Blackshear et al. | 604/141 |
| 3,923,060 | 12/1975 | Ellinwood, Jr. | 604/891.1 |
| 4,086,816 | 5/1978 | Jon et al. | 73/587 |
| 4,193,397 | 3/1980 | Touler et al. | 604/56 |
| 4,317,368 | 3/1982 | McElroy | 73/587 |
| 4,550,603 | 11/1985 | Fukada et al. | 73/587 |
| 4,550,604 | 11/1985 | Sugimoto et al. | 73/587 |
| 4,619,653 | 10/1986 | Fischell | 604/891.1 |
| 4,731,051 | 3/1988 | Fischell | 604/67 |
| 4,884,449 | 12/1989 | Nishimoto et al. | 73/587 |
| 4,985,015 | 1/1991 | Obermann et al. | 604/67 |
| 5,005,415 | 4/1991 | Holroyd | 73/587 |
| 5,029,474 | 7/1991 | Schulze | 73/587 |
| 5,064,412 | 11/1991 | Henke et al. | 604/67 |

Primary Examiner—C. Fred Rosenbaum
Assistant Examiner—Manuel Mendez
Attorney, Agent, or Firm—Leslie S. Miller

[57] ABSTRACT

Apparatus located in an implantable medication infusion pump for quickly and easily detecting a condition adversely affecting medication delivery in the implantable medication infusion pump is disclosed which can reliably detect occurrences including an occluded catheter, the presence of air in the pumping mechanism, and the failure of the pumping mechanism. The system uses the amplitude of an acoustic signal generated by operation of the pumping mechanism as compared with a baseline signal to detect an encapsulated or occluded catheter or air in the fluid line. In addition, the system can detect a partially encapsulated or occluded catheter by detecting repeated downward slope patterns during repetitive, closely spaced pumping cycles.

35 Claims, 5 Drawing Sheets

IMPLANTABLE MEDICATION INFUSION PUMP INCLUDING SELF-CONTAINED ACOUSTIC FAULT DETECTION APPARATUS

This is a continuation of co-pending application Ser. No. 07/718,709 filed on Jun. 21, 1991 now abandoned.

IDENTIFICATION OF RELATED PATENT APPLICATION

This application is related to another concurrently filed copending patent application, namely U.S. Ser. No. 719,221, which is entitled "Method and Apparatus for Acoustic Fault Detection in an Implantable Medication Infusion Pump." That application is hereby incorporated herein by reference.

BACKGROUND OF THE INVENTION

Field of the Invention.

This invention relates generally to apparatus located in an implantable medication infusion pump for quickly and easily detecting a condition adversely affecting medication delivery in the implantable medication infusion pump, and more particularly to such an apparatus and method for reliably detecting occurrences including an occluded catheter, the presence of air in the pumping mechanism, and the failure of the pumping mechanism.

Medication infusion pumps are generally known in the art for use in delivering a selected medication to a patient in a scheduled or preprogrammed manner. In recent years, such medication infusion pumps have been developed in compact form adapted for implantation into the body of a patient. They are used to deliver a specific medication such as insulin to the patient in discrete (but essentially continuous) doses over an extended time period.

An implantable medication infusion pump of this general type typically includes an internal medication reservoir for receiving and storing a supply of the selected medication in liquid form. Other components incorporated in the device include a power source (typically a battery), a miniature pumping mechanism, and associated electronic programmed control means for delivering the medication to the patient according to a prescribed schedule. For one illustrative example of an implanted or implantable medication infusion pump of this general type, see U.S. Pat. No. 4,573,994, to Fischell.

Implantable medication infusion pumps are normally equipped with an inlet port through which fluid medication can be supplied to permit periodic refilling of the pump reservoir. This inlet port is typically positioned and shaped for receiving a transcutaneous needle through which the fluid medication is supplied from outside the patient's body. Accordingly, the pump reservoir can be filled or refilled without requiring surgical removal from the patient's body, and further without requiring any other significant surgical procedure.

The output port of an implantable medication infusion pump is typically connected to the proximal end of a catheter. The distal end of the catheter is located in the abdominal cavity, where it may either be free-floating or implanted in the tissue of the omentum. If the distal end is to be free-floating, which is currently seen as the better technique, an intermediate portion of the catheter having a 90 degree bend therein is anchored to the peritoneal wall. If the distal end is to be placed into a fold in the omentum tissue, the tissue is sutured around the distal end of the catheter. The medication is thus delivered by the implantable medication infusion pump through the catheter to the body of patient.

While implantable, refillable medication infusion pumps constitute a major step forward in reliable and convenient administration of certain medications, there are several conditions which may be encountered which are difficult to detect, and which may impede the efficacious delivery of medication to the patient. The most significant of these problems is the problem of a partially or completely blocked catheter. This is typically caused by one of two blocking mechanisms: first, by tissue growth encapsulating substantially the entire distal end of the catheter to form a "sock;" or secondly, by deposits aggregating inside the lumen of the catheter to block or occlude the lumen of the catheter. Either of these conditions may result in the flow of medication from the catheter being partially or fully obstructed.

A catheter may become partially encapsulated or occluded, which will act to raise the pressure in the catheter when medication is being delivered. More infrequently, a catheter may become virtually fully encapsulated or occluded, essentially preventing the medication from flowing from the distal end of the catheter. Such a condition will defeat the intended purpose of the implanted system by substantially preventing it from delivering medication.

In delivering medications such as insulin, periodic relatively larger doses (boluses) are periodically supplied as needed (such as immediately before meals) in addition to an essentially continuous supply of the medication at a low rate (basal rate). With a partially obstructed catheter, the delivery of medication at the basal rate may not be a problem, while the delivery of a larger bolus may cause pressure to build to a point where delivery is significantly impeded. It will be recognized by those skilled in the art that nondelivery of medication due to a catheter obstruction thus represents a significant problem.

Another problem encountered by implantable medication infusion pumps is the presence of a gas bubble in the pumping mechanism. This is a particularly serious problem in medication infusion pumps which are incapable of pumping gas. Still another problem is that of pump failure, in which the pumping mechanism simply stops working for whatever reason. These problems, like the problem of catheter obstruction, may result in vital medication not being delivered to a patient.

At present, the lack of medication being delivered to a patient is generally detected by physiological measures. Such measures, for example, may include blood glucose analysis (for insulin), surgical procedures such as laparoscopy, or the use of an invasive pressure measuring technique such as a side port. These measures are all effective at diagnosis only significantly after the problem has been encountered for some time. In the case of a partially obstructed catheter, these techniques may not be successful in making a correct diagnosis.

A promising development has been the use of an acoustic sensor built into the pumping mechanism of the implantable medication infusion pump, which is taught in U.S. Pat. No. 4,985,015, to Obermann et al. (the '015 patent), which patent is hereby incorporated herein by reference. This device uses a piezo element located in the pumping mechanism to sense noise, with the noise sensed (or not sensed) providing information about medication infusion pump operation. The '015 patent teaches that the amplitude and timing of the acoustic signal present information useful to diagnosis of various pumping conditions.

Specifically, with regard to the timing of a "normal" signal the '015 patent teaches that an empty reservoir is indicated when the signal is greatly premature, and that air bubbles in the pumped fluid are indicated when the signal is slightly premature. With regard to the amplitude of the acoustic signal, the '015 patent teaches an amplitude or threshold discriminator which produces a signal when the medication infusion pump is operating properly, and no signal when the catheter is occluded. In the event of a catheter occlusion beginning to occur, there will be a signal when pumping is started, which signal will disappear when pumping at a high rate (read pumping a bolus).

Thus, the '015 patent teaches the use of a threshold detected acoustic signal, the timing and presence of which provides operational information on the system. This is certainly a significant improvement in the detection of the problems mentioned above. However, the system of the '015 patent has certain disadvantages representing opportunities for improvement in the art.

The '015 patent uses a threshold detection system which is incapable of detecting whether no signal detected is indicative of an occlusion or pump failure. This is highly significant, since it would be undesirable to perform a surgery to replace a catheter when the catheter is fine and the medication infusion pump is not operating properly.

It is accordingly the primary objective of the present invention that it provide an improved apparatus located in the implanted medication infusion pump and an associated method for detecting the problems mentioned above in the implanted medication infusion pump. The apparatus and method for detecting problems in the implanted medication infusion pump must be capable of discriminating between problems such as an encapsulated or occluded catheter and a nonoperational pumping mechanism. It is yet another objective that the apparatus and method of the present invention be capable of determining the presence of air in the system. The apparatus and method of the present invention must therefore allow a correct diagnosis of problems to be made with a high degree of accuracy while avoiding entirely an incorrect diagnosis which could result in the removal of a properly functioning system.

The apparatus and method for detecting problems in an implanted medication infusion pump must also avoid interference with spurious signals. The apparatus should not add significantly to the cost of manufacturing the implantable medication infusion pump. In addition, a means should be provided to enable the analysis to be tailored to individual patients, to better follow the conditions of these patients. It is also an objective that all of the aforesaid advantages and objectives be achieved without incurring any substantial relative disadvantage.

SUMMARY OF THE INVENTION

It has been established by Obermann et al. in the '015 patent by that by using an acoustic sensor in an implanted medication infusion pump, an acoustic signal will be provided when the pumping mechanism, typically a piston-type pump, operates. This signal in the '015 patent is phase and level detected, and has been found to be indicative, to the extent of the limitations discussed above, of the state of the implanted system. The present invention improves substantially on the basic concept by performing a more complete analysis on the level of the signal, rejecting the essentially digital level detection of the '015 patent for a more complete analysis which will yield more complete information as to the state of the system.

The signal is analyzed by circuitry within the implanted medication infusion pump, either in the time domain or in the frequency domain (or in both). The signal obtained for a system with an encapsulated or occluded catheter is significantly smaller than the signal for a "normal" system. In addition, it has been determined that the signal obtained for a system with air contained in the pumping path is substantially larger than the signal for a "normal" system. These fundamental facts are true both in the time domain and in the frequency domain. Thus, by storing appropriate baseline values in memory within the implanted medication infusion pump, and later comparing these stored baseline values with corresponding values measured later, the condition of the implanted medication infusion system may be evaluated.

In the preferred embodiment, the value utilized in the time domain is the peak voltage, and in the frequency domain is the peak sound level at the peak frequency. RMS values or other average values may also be utilized. Alternately, the sound level at a particular frequency may be used in the frequency domain. In addition, the integral of the sound level in the frequency domain or the integral of the magnitude of the voltage in the time domain (or their averages, which are proportional to the integrals) may be used. All of these indicia have been demonstrated to provide a clear indication of the state of the system.

Partial encapsulations or occlusions may also be diagnosed by monitoring successive signals with the implanted medication infusion system delivering medication with a rapid sequence of pump strokes. Over a sequence of rapid, successive pump strokes a falling acoustic level is indicative of a partial encapsulation or occlusion.

As mentioned above, in the preferred embodiment the baseline reading of the implanted medication infusion pump is utilized to provide a means for a comparison. The baseline readings of a given patient may vary widely, due to different physiological elements such as weight of the patient and implantation location. The comparison of readings from a malfunctioning system with the baseline readings will provide a dramatic indication of the efficacy of the comparison in diagnosing pump problems (or the lack thereof).

The preferred embodiment also included an interconnection between the monitoring system of the present invention and the control circuitry of the implanted medication infusion pump. In the event of a problem, an alarm can be provided through known means such as low level "tickle" electrical stimulation of the patient, a buzzer, and/or through telemetry to the patient and physician communicators. If desired, the system may also be shut down.

It may therefore be seen that the present invention teaches an improved apparatus located in the implanted medication infusion pump and an associated method for detecting the problems mentioned above in the implanted medication infusion pump. The apparatus and method of the present invention is capable of discriminating between problems such as an encapsulated or occluded catheter and a nonoperational pumping mechanism. It is also capable of determining the presence of air in the system. The apparatus and method is highly accurate in detecting problems in the implanted system, and allows a correct diagnosis of problems to be made with a high degree of accuracy while avoiding entirely an incorrect diagnosis which could result in the removal of a properly functioning system.

The apparatus and method for detecting problems in an implanted medication infusion pump avoids interference with spurious signals by filtering. The apparatus does not add significantly to the cost of manufacturing the implantable medication infusion pump. In addition, by obtaining baseline data the analysis is specifically tailored to individual patients, to thereby better follow the conditions of these patients.

Other features and advantages of the present invention will become more apparent following a detailed description of the preferred implementation of the present invention. All of the aforesaid advantages and objectives of the present invention are achieved without incurring any substantial relative disadvantage.

DESCRIPTION OF THE DRAWINGS

The advantages of the present invention are best understood with reference to the drawings, in which.

DETAILED DESCRIPTION OF THE PREFERRED EMBODIMENT

Figure 1:
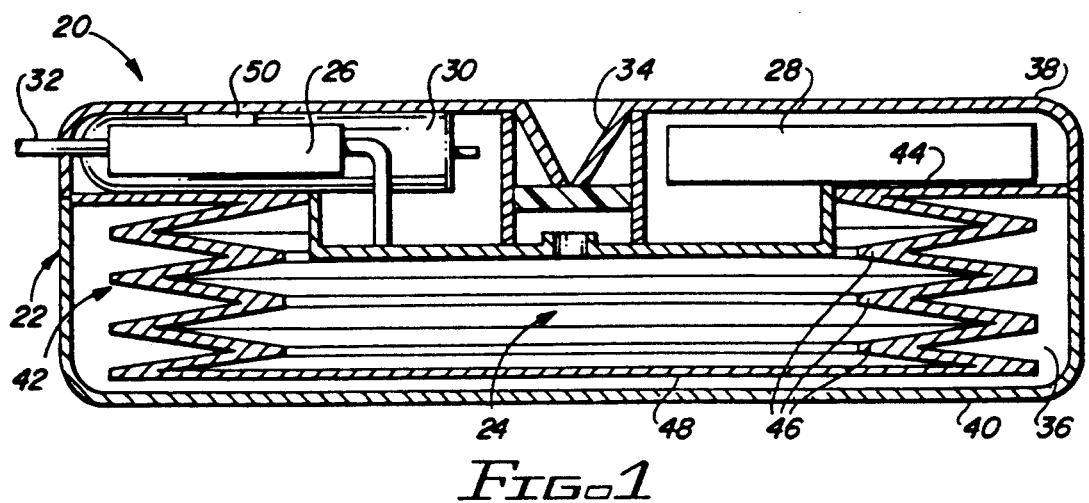
FIG. 1 is a cutaway view of an implantable medication infusion pump incorporating the present invention.

An illustrative medication infusion pump 20, shown in FIG. 1, comprises a small and substantially self-contained unit designed for direct implantation into the body of a patient. The medication infusion pump 20 comprises a hermetically sealed pump housing 22 constructed from a biocompatible material such as titanium or titanium alloy. The bottom portion of the hermetically sealed pump housing 22 defines the internal medication reservoir 24 for receiving and storing the supply of the selected medication in liquid form, such as insulin for a diabetic patient.

The hermetically sealed pump housing 22 further encases a miniature dispensing pump 26 and generally depicted associated electronic control circuitry 28 in combination with a battery 30 for periodically operating the pump 26 to deliver medication doses from the reservoir 24 to the patient via an appropriate catheter 32 or the like. The general control circuitry includes circuitry which is suitably preprogrammed to deliver the medication in accordance with individual patient need. An inlet or refill port 34 on the hermetically sealed pump housing 22 is adapted to receive a hypodermic needle (not shown) to permit percutaneous refilling of the reservoir 24 without requiring surgical access to the medication infusion pump 20. For a more detailed description of the overall construction and operation of implantable infusion pumps of this general type, see U.S. Pat. Nos. 4,373,527 and 4,573,994, both to Fischell, both of which are hereby incorporated herein by reference.

As is known in the art, the medication infusion pump 20 includes the variable volume pressure reservoir 36 mounted within the hermetically sealed pump housing 22 with at least one movable wall of the pressure reservoir 36 being shared with and thereby defining at least a portion of the reservoir 24. More particularly, the pressure reservoir 36 contains a selected pressure fluid adapted to vary the volumetric size of the reservoir 24 in accordance with the quantity of medication therein to maintain the medication under substantially constant pressure conditions.

The preferred pressure fluid is a fluorocarbon which has a substantially linear pressure characteristic as it changes from liquid to vapor state and vice versa at normal human body temperature and at a normal range of altitudes. A preferred pressure fluid is Freon 113 which assumes a liquid-vapor state at normal body temperature and at altitudinal variations up to about 8,500 feet above sea level to exert a slightly negative and substantially constant pressure of approximately $-1.0$ to $-4.5$ psi on the reservoir 24. A positive pressure reservoir could instead be used.

The illustrative drawings show the assembled hermetically sealed pump housing 22 in the form of interfitting upper and lower housing members 38 and 40 of generally circular and shell-shaped configuration. In general terms, the upper housing member 38 has the pump 26 and the general control circuitry with the associated battery 30 installed therein. By contrast, the lower housing member 40 has a bellows unit 42 installed therein. The bellows unit 42 is shown with an upper ring 44 of generally annular shape having an outer periphery secured in sealed relation to an inboard side of a circular wall on the lower housing member 40, and an inner periphery joined to a plurality of downwardly extending bellows corrugations 46.

The bellows corrugations 46 of the bellows unit 42 are joined in turn to a circular lower plate 48. This structure defines a pump reservoir subassembly with the volumetric space disposed radially within the bellows unit 42 defining the reservoir 24, and the volumetric space located radially outside and axially below the bellows unit 42 defining the pressure reservoir 36. When the medication infusion pump 20 is finally assembled, it will be understood that the upper housing member 38 fits over the lower housing member 40 to define and close the upper region of the reservoir 24 in operative relation with the pump 26.

The only component of the present invention which is visible in FIG. 1 is an acoustic transducer 50, which is in the preferred embodiment mounted between the pump 26 and the upper housing member 38. The acoustic transducer 50 in the preferred embodiment is a piezoelectric element, such as a segment of Kynar which is mounted on the pump 26. When the pump 26 pulses, the piezo sensor 50, as it will hereafter be called, will generate an electrical signal indicative of the acoustic signal generated by the pulsing of the pump 28. It will be understood that the general control circuitry includes additional elements of the present invention, as will become apparent below.

Figure 2:
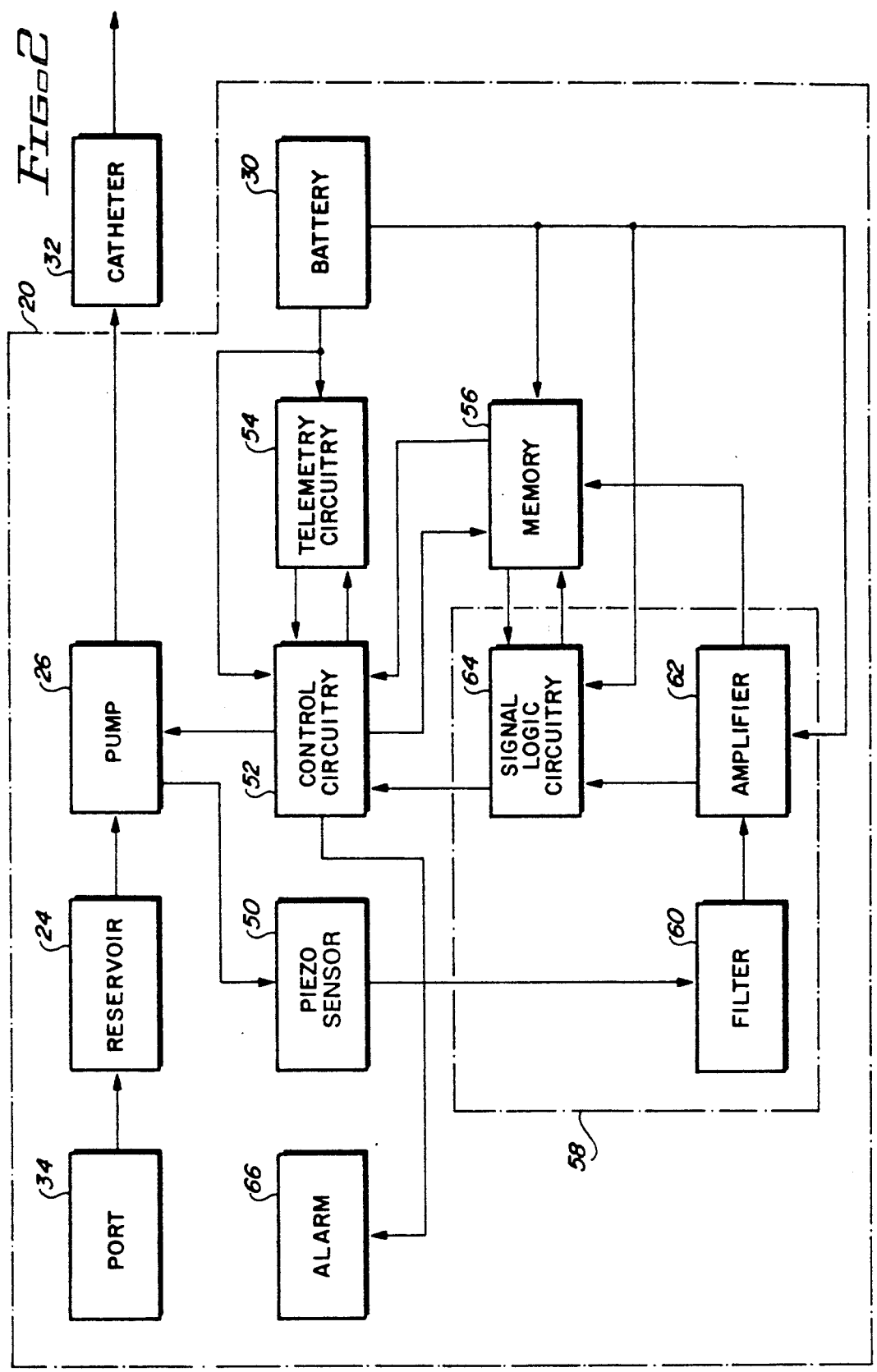
FIG. 2 is a block diagram illustrating in schematic fashion the system illustrated in FIG. 1, with particular attention to the components of the acoustic monitoring system of the present invention.

Referring next to FIG. 2, a block diagram illustrating how the components of the present invention are configured is presented. The fluid path from the port 34 to the reservoir 24, from the reservoir 34 to the pump 26, and from the pump 26 to the catheter 32 are illustrated. The pump 26 mechanically drives the piezo sensor 50 to produce an electrical output.

The general control circuitry 28 of FIG. 1 is illustrated in FIG. 2 as four elements: control circuitry 52 for operations of the pump as is generally known in the art; telemetry circuitry 54, also known in the art; memory 56, also known in the art; and processing circuitry 58 for processing the signal from the piezo sensor 50. The telemetry circuitry 54 is connected to send data to and to receive data from the control circuitry 52. The control circuitry 52 is connected to drive the pump 26. The electrical output from the piezo sensor 50 is supplied to the processing circuitry 58, which supplies an output signal to the control circuitry 52.

The processing circuitry 58 includes a filter 60, which filters the electrical signal from the piezo sensor 50. The filtered signal from the piezo sensor 50 is supplied to an amplifier 62, which supplied the amplified filtered signal from the piezo sensor 50 to signal logic circuitry 64 and to the memory 56. The output from the signal logic circuitry 64 is the output signal of the processing circuitry 58, which is supplied to the control circuitry 52.

The memory 56 is connected to receive data from and to send data to both the signal logic circuitry 64 and the control circuitry 52. The battery is connected to power the entire system, including the control circuitry 52, the telemetry circuitry 54, the memory 56, the amplifier 62, and the signal logic circuitry 64. An alarm mechanism 66 may be included to provide an indication of a system malfunction.

In operation, the present invention uses the piezo sensor 50 to produce a signal each time the pump 26 is operated. The pump 26, which is typically a piston-type pump, will produce an acoustic signal whenever it is operated. In response, the piezo sensor produces an output signal each time the pump 26 is pulsed.

The filter 60 preferably includes a high pass filter which cuts off the portion of the signal below 1000 Hz. This eliminates body noise, which has been found to be necessary for proper signal discrimination. The preferred embodiment is a bandbass filter passing signals between 1000 Hz and 5000 Hz.

The signal from the piezo sensor 50 is thus filtered by the filter 60, and is then amplified by the amplifier 62. At this point, a voltage waveform representative of the acoustic signal generated by the pump 26 exists, which may be stored in the memory 56. This signal is also supplied to the signal logic circuitry 64, where it is analyzed.

At this point it is necessary to note that a number of different analyses may be performed. The basic analysis is a comparison between the baseline voltage signal and the current voltage signal. It has been determined that a signal from a system which is "normal" has a first value in the time domain. A system with an encapsulated or occluded catheter 32 has a value in the time domain which is at a substantially lower level than the "normal" signal. A system with air in the fluid line has a value in the time domain which is at a higher level than the "normal" signal.

Figure 3:
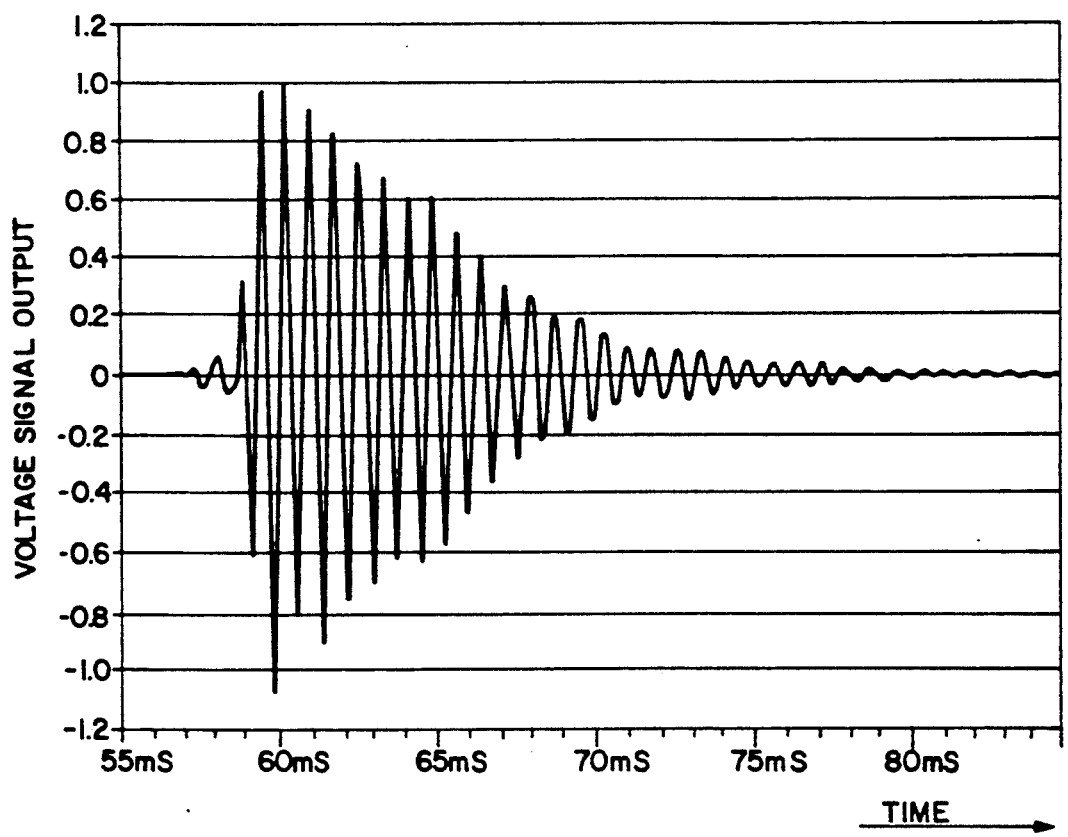
FIG. 3 is a waveform illustrating the filtered, amplified signal from the acoustic sensor in the time domain for a normally operating implanted medication infusion system.
Figure 4:
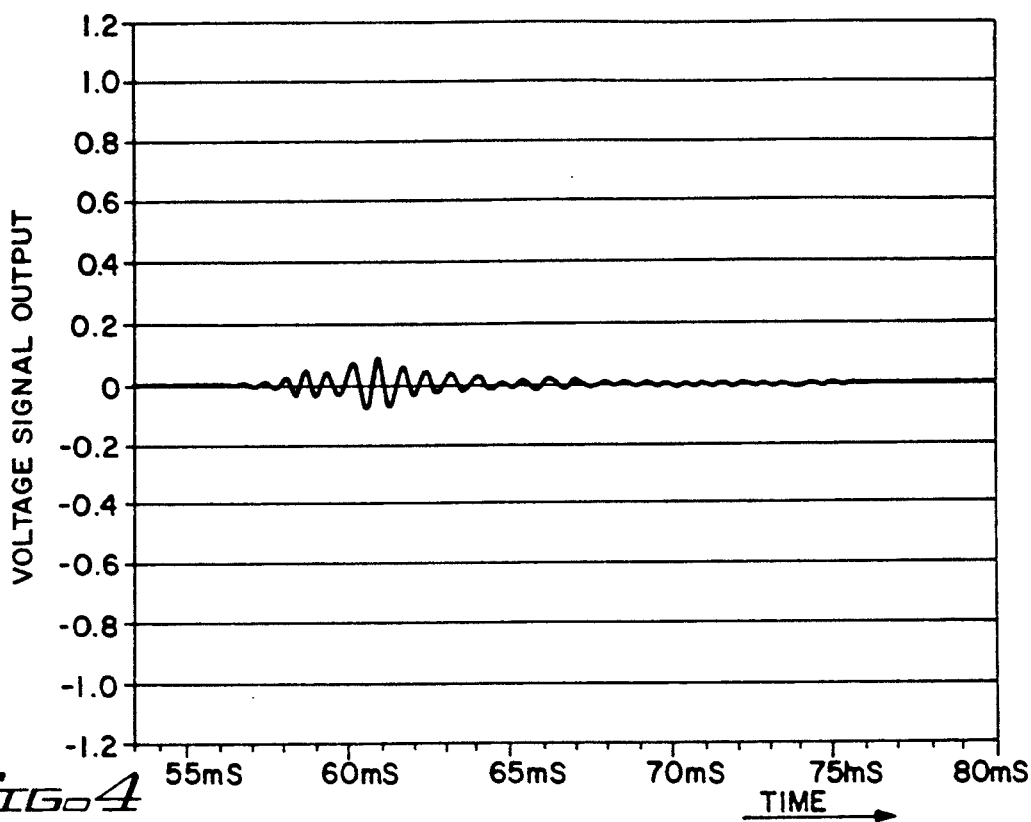
FIG. 4 is a waveform illustrating the filtered, amplified signal from the acoustic sensor in the time domain for an implanted medication infusion system having a completely encapsulated or occluded catheter.

The preferred embodiment uses the peak voltage signal as the sensed parameter. Thus, a system with an encapsulated or occluded catheter 32 has a peak voltage in the time domain which is substantially lower than the peak voltage of the "normal" signal in the time domain. This is apparent in comparing FIGS. 3 and 4. FIG. 3 shows the time domain waveform for a "normal" system, while FIG. 4 shows the time domain waveform for an encapsulated or occluded catheter 32. The signals, including the peak signal, are over ten times higher for a "normal" system than for a system with an encapsulated or occluded catheter 32. As a cautious minimum, when the current signal is one-fifth of the baseline signal or less, an encapsulated or occluded catheter is indicated.

In addition, a system with air in the fluid line has a peak voltage in the time domain which is higher than the peak voltage of the "normal" signal in the time domain. The peak signal in the time domain for a system with air in the fluid line is two to three times greater than the peak voltage in the time domain for a "normal" system. As a cautious minimum, when the current signal is twice the baseline signal or more, air in the fluid line is indicated.

In the time domain, the average, the RMS average, or the integral of the voltage signal could also be used instead.

In addition, the frequency content of the signal could be used instead. If the frequency domain of the signals are calculated (using a FFT in the signal logic circuitry 64), the peak value of the frequency domain signals has also been found to be indicative of the condition of the system.

Figure 5:
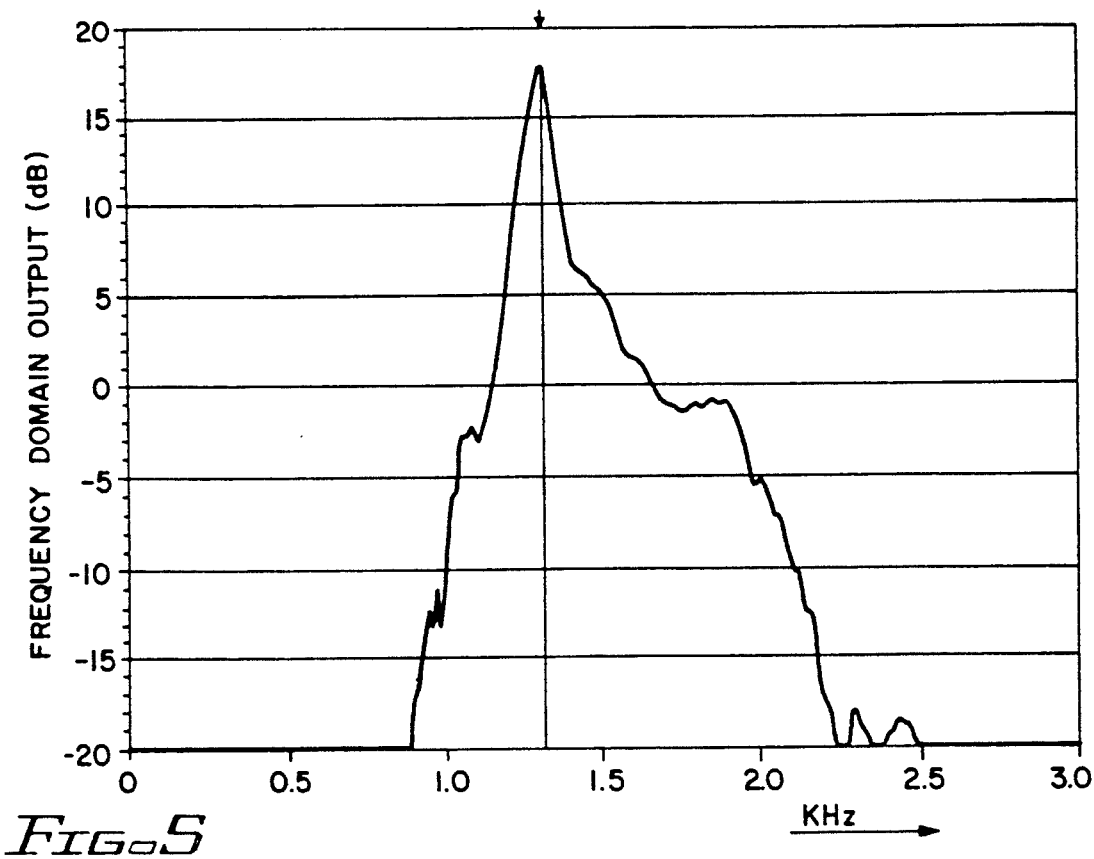
FIG. 5 is a waveform illustrating the filtered, amplified signal from the acoustic sensor in the frequency domain for a normally operating implanted medication infusion system.
Figure 6:
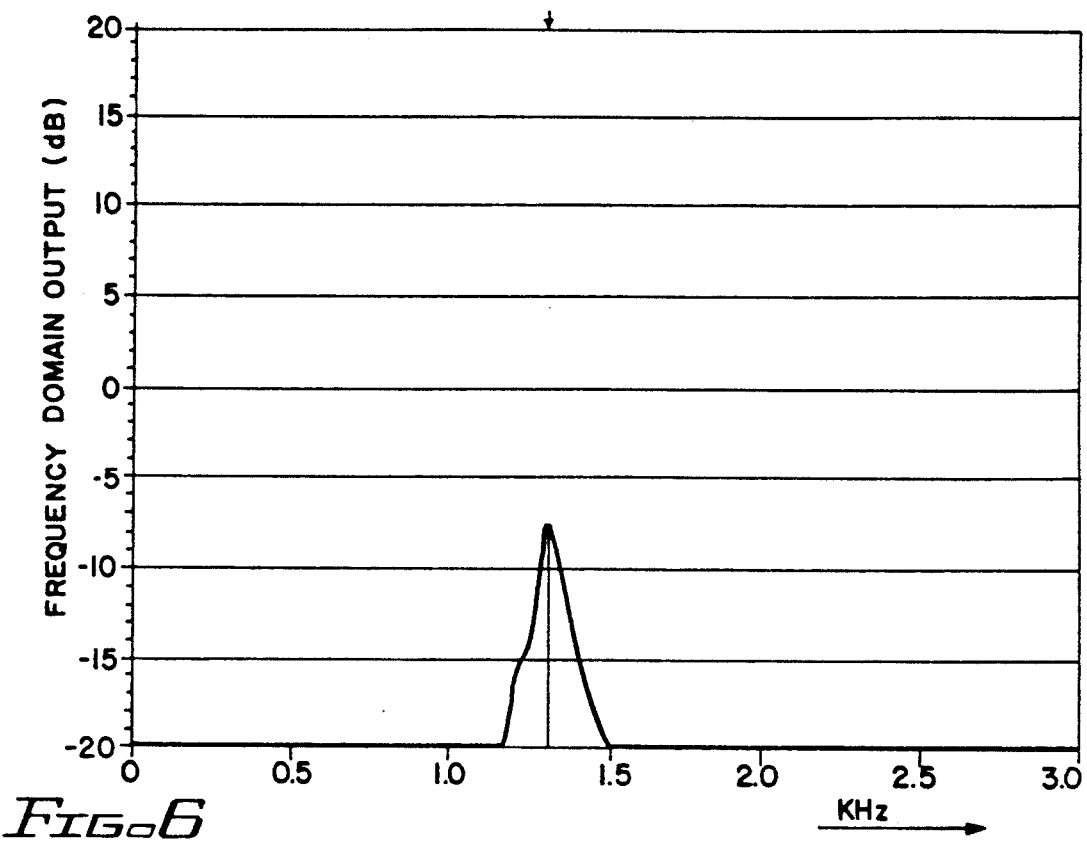
FIG. 6 is a waveform illustrating the filtered, amplified signal from the acoustic sensor in the frequency domain for an implanted medication infusion system having a completely encapsulated or occluded catheter.

Thus, a system with an encapsulated or occluded catheter 32 has a peak value in the frequency domain which is substantially lower than the peak value of the "normal" signal in the frequency domain. This is apparent in comparing FIGS. 5 and 6. FIG. 5 shows the frequency domain waveform for a "normal" system, while FIG. 6 shows the frequency domain waveform for an encapsulated or occluded catheter 32. The signals, including the peak signal, are over 20 dB higher for a "normal" system than for a system with an encapsulated or occluded catheter 32.

Figure 7:
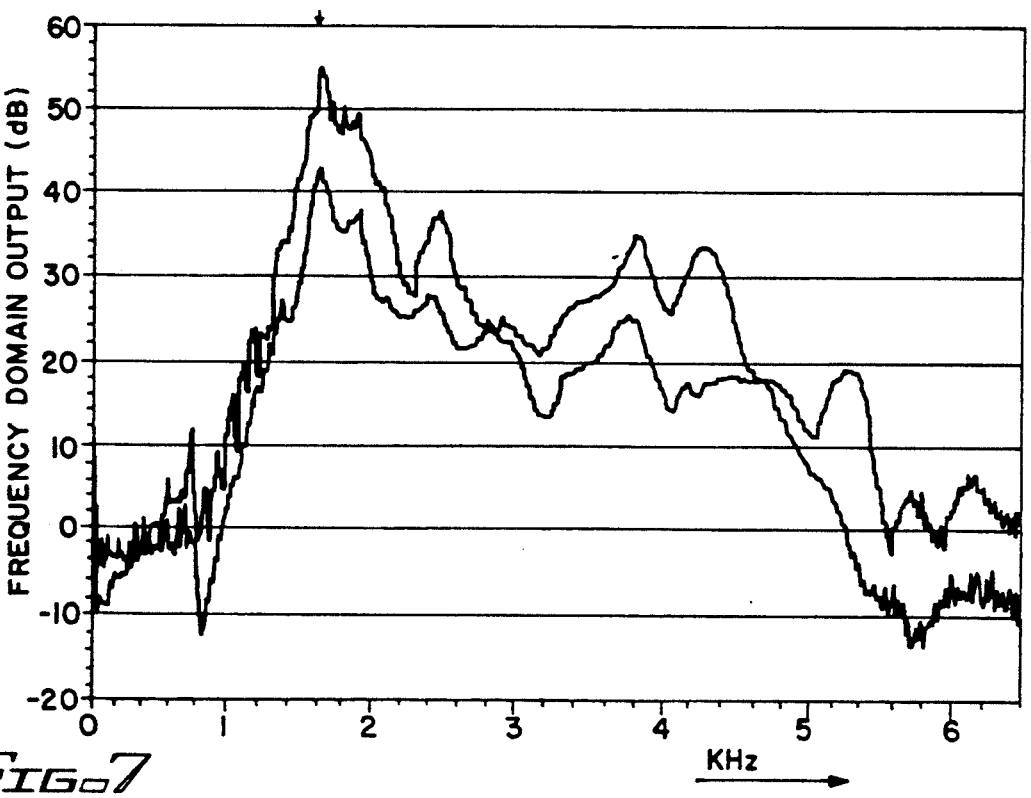
FIG. 7 illustrates for comparison a waveform illustrating the filtered, amplified signal from the acoustic sensor in the frequency domain for a normally operating implanted medication infusion system, and a waveform illustrating the filtered, amplified signal from the acoustic sensor in the frequency domain for an implanted medication infusion system having air in the fluid line.

In addition, a system with air in the fluid line has a peak value in the frequency domain which is 5 to 10 dB higher than the peak value of the "normal" signal in the frequency domain. This is illustrated in FIG. 7. The upper waveform in FIG. 7 is for a system with air in the fluid line, and the lower waveform is for a "normal" system. It is apparent that the peak signal in the time domain for a system with air in the fluid line is 2 to 3 times greater than the peak voltage in the time domain for a "normal" system.

In the frequency domain, the value at a particular frequency could also be used instead of the peak value. Here, that frequency would be approximately 1320 Hz; typically, it is between 1200 Hz and 1700 Hz. In addition, the average, the RMS average, or the integral of the signal could also be used instead.

Figure 8:
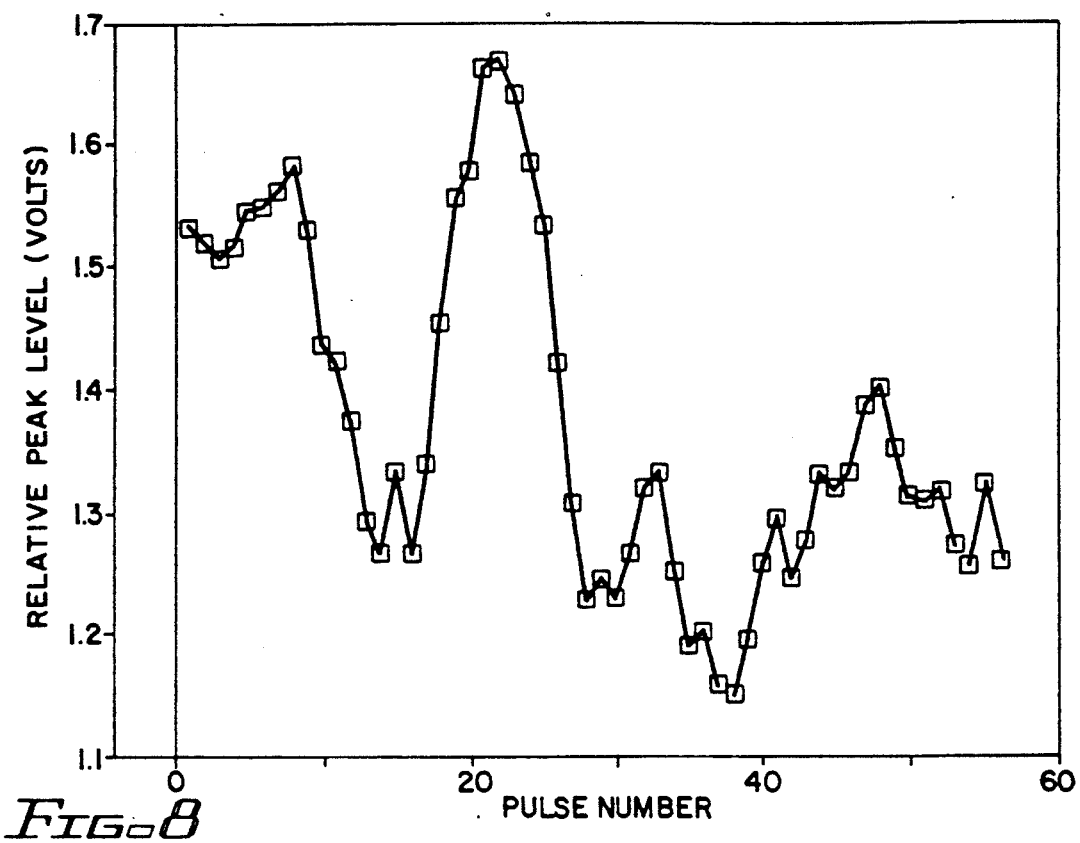
FIG. 8 is a waveform illustrating the relative peak level of the filtered, amplified signal from the acoustic sensor for an implanted medication infusion system having a partially encapsulated or occluded catheter plotted against pulses of fluid which the system is continuously delivering.
Figure 9:
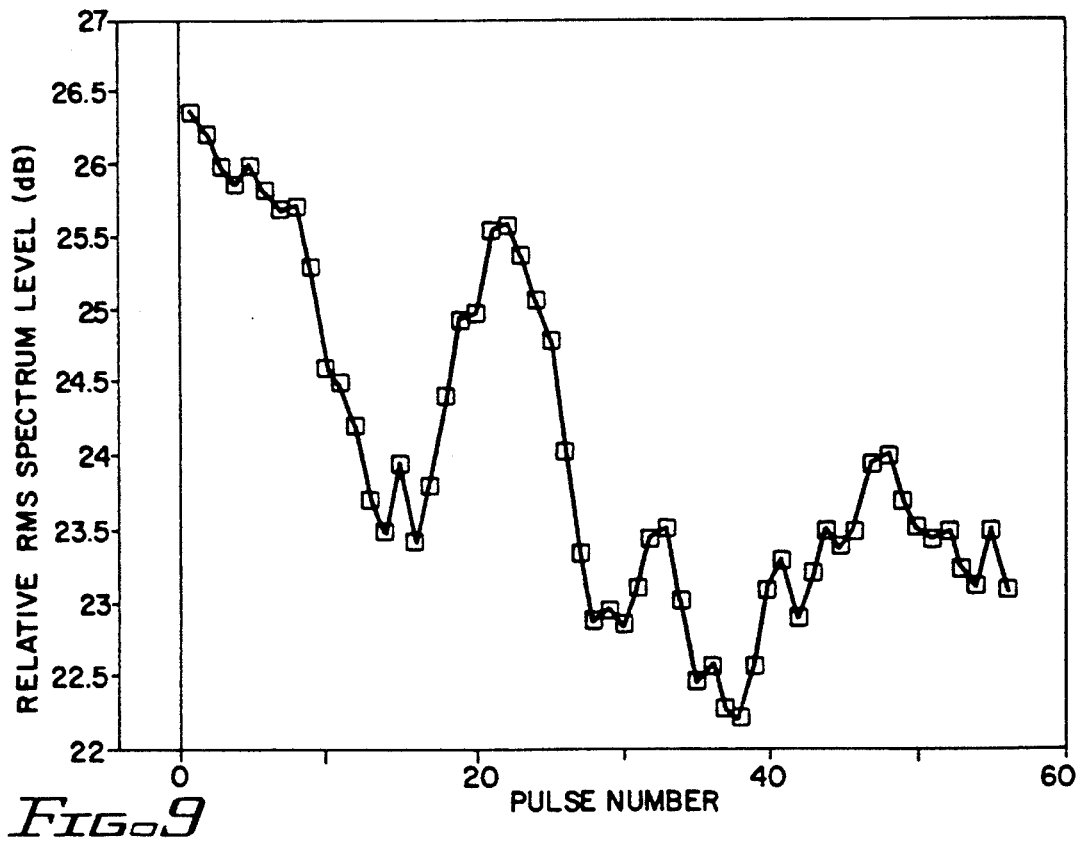
FIG. 9 is a waveform illustrating the relative RMS spectrum level of the filtered, amplified signal from the acoustic sensor for an implanted medication infusion system having a partially encapsulated or occluded catheter plotted against pulses of fluid which the system is continuously delivering.

A partially encapsulated or occluded catheter 32 may also be diagnosed, either in the time domain as shown in FIG. 8, or in the frequency domain as shown in FIG. 9. By plotting the peak time domain voltage versus pulses of the pump 26 (FIG. 8), or relative RMS spectrum level versus pulses of the pump 26 (FIG. 9), patterns emerge. There will be a downward slope of the plot in either case, indicating an encapsulation or occlusion, until the encapsulation or occlusion opens up, at which time the plot will slope upwards until pressure builds up again. Thus, a single or repeated downward slope while pumping during a bolus indicates a partial encapsulation or occlusion. As a cautious minimum, when repeated downward slope patterns are observed during repetitive, closely spaced pumping cycles, a partially encapsulated or occluded catheter is indicated.

Specifically, when the current signal is one-fifth of the baseline signal or less, an encapsulated or occluded catheter is indicated. When the current signal is twice the baseline signal or more, air in the fluid line is indicated. When repeated downward slope patterns are observed during repetitive, closely spaced pumping cycles, a partially encapsulated or occluded catheter is indicated. Of course, if there is no signal at all, an inoperative pump 26 is indicated.

In operation, when the implantable medication infusion pump 20 is first implanted, the system will build up baseline values indicative of proper operation. These baseline values will be stored in the memory 56. Later, as the device operates and as current values are generated, the signal logic circuitry 64 will compare these new values with the stored baseline values. A conclusion may thus be made as to the state of the system.

A current signal which is substantially lower than the baseline signal is indicative of an encapsulated or occluded catheter. A current signal which is significantly higher than the baseline signal is indicative of air in the fluid line. A current signal for a sequence of pulses which decrease in amplitude (either in a single sequence or in repeated sequences with brief returns to higher values) is indicative of a partially encapsulated or occluded catheter.

If desired, the memory 56 may be used to periodically store values of the signals at different times. This information may be telemetered out later to review whether there is a trend indicating that an encapsulation or occlusion in the catheter 32 is about to occur.

If the system is operating improperly, an alarm may be given through conventional means, designated generally in FIG. 2 as the alarm mechanism 66. Examples of such means include built-in alarms (included within the control circuitry 52) such as a low level "tickle" electrical stimulation of the patient or a buzzer, or through telemetry to patient and physician communicators (not shown). If desired, the system may also be shut down by the control circuitry 52.

It may therefore be appreciated from the above detailed description of the preferred embodiment of the present invention that it teaches an improved apparatus located in the implanted medication infusion pump and an associated method for detecting the problems mentioned above in the implanted medication infusion pump. The apparatus and method of the present invention is capable of discriminating between problems such as an encapsulated or occluded catheter and a nonoperational pumping mechanism. It is also capable of determining the presence of air in the system. The apparatus and method is highly accurate in detecting problems in the implanted system, and allows a correct diagnosis of problems to be made with a high degree of accuracy while avoiding entirely an incorrect diagnosis which could result in the removal of a properly functioning system.

The apparatus and method for detecting problems in an implanted medication infusion pump avoids interference with spurious signals by filtering. The apparatus does not add significantly to the cost of manufacturing the implantable medication infusion pump. In addition, by obtaining baseline data the analysis is specifically tailored to individual patients, to thereby better follow the conditions of these patients. Finally, all of the aforesaid advantages and objectives are achieved without incurring any substantial relative disadvantage.

Although an exemplary embodiment of the present invention has been shown and described, it will be apparent to those having ordinary skill in the art that a wide variety of changes, modifications, alterations, or improvements to the invention as described herein may be made, none of which depart from the spirit of the present invention. All such changes, modifications, and alterations should therefore be seen as within the scope of the present invention.

What is claimed is:

1. An implantable medication infusion pump including apparatus for diagnosing a system malfunction, comprising:

a reservoir for containing a fluid medication;

means for transferring said fluid medication from said reservoir to a location outside said implantable medication infusion pump;

means located in said implantable medication infusion pump adjacent to said transferring means for generating electrical signals proportional to acoustic signals generated by said transferring means;

means for processing said electrical signals to produce processed electrical signals;

logic means for utilizing a characteristic related to the relative amplitude of said processed electrical signals to determine the operational condition of the implanted medication infusion pump, said logic means providing a first informational signal if said processed electrical signals are greater than or equal to a first predetermined value, said logic means providing a second informational signal if said processed electrical signals are smaller than or equal to a second predetermined value, said second predetermined value being smaller than said first predetermined value; and means for providing an informational signal if said logic means determines the existence of a system malfunction.

2. An implantable medication infusion pump as defined in claim 1, wherein said transferring means comprises:
a piston-type pump.

3. An implantable medication infusion pump as defined in claim 1, wherein said generated means comprises:
a transducer mounted inside said implantable medication infusion pump adjacent to said transferring means.

4. An implantable medication infusion pump as defined in claim 3, wherein said transducer comprises:
a piezoelectric element mounted to pick up acoustic signals generated by said transferring means.

5. An implantable medication infusion pump as defined in claim 4, wherein said piezoelectric element comprises:
a Kynar element.

6. An implantable medication infusion pump as defined in claim 1, wherein said processing means comprises:
a filter to filter said electrical signals.

7. An implantable medication infusion pump as defined in claim 6, wherein said filter comprises:
a high pass filter to substantially eliminate body noises in said electrical signals.

8. An implantable medication infusion pump as defined in claim 7, wherein said high pass filter removes signals below approximately 1 KHz.

9. An implantable medication infusion pump as defined in claim 7, wherein said filter additionally comprises:
a low pass filter to remove signals above approximately 5 KHz from said electrical signals.

10. An implantable medication infusion pump as defined in claim 6, wherein said processing means additionally comprises:
an amplifier to amplify said electrical signals.

11. An implantable medication infusion pump as defined in claim 1, wherein said logic means comprises:
means for determining a characteristic related to the relative amplitude of said processed electrical signals; and
means for comparing said characteristic related tot he relative amplitude of said processed electrical signals to a characteristic of baseline electrical signals related to their relative amplitude to determine the operational condition of the implanted medication infusion pump, said first predetermined value being substantially larger than the characteristic of said baseline electrical signals related to their relative amplitude, said second predetermined value being substantially smaller than the characteristic of said baseline electrical signals related to their relative amplitude.

12. An implantable medication infusion pump as defined in claim 11, wherein said comparing means indicates an encapsulated or occluded catheter when the relative amplitude of said processed electrical signals is smaller than or equal to said second predetermined value.

13. An implantable medication infusion pump as defined in claim 12, wherein said comparing means indicates an encapsulated or occluded catheter when the relative amplitude of said processed electrical signals is approximately one-fifth of the relative amplitude of said baseline electrical signals or less, said second predetermined value thus being approximately one-fifth of the amplitude of said baseline electrical signals.

14. An implantable medication infusion pump as defined in claim 11, wherein said comparing means indicates the presence of air in the fluid line when the relative amplitude of said processed electrical signals is larger than or equal to said first predetermined value.

15. An implantable medication infusion pump as defined in claim 12, wherein said comparing means indicates the presence of air in the fluid line when the relative amplitude of said processed electrical signals is approximately twice the relative amplitude of said baseline electrical signals or more, said first predetermined value thus being approximately twice the amplitude of said baseline electrical signals.

16. An implantable medication infusion pump as defined in claim 11, wherein the characteristics of said processed electrical signals and said baseline electrical signals related to their relative amplitudes comprise:
the peak voltage in the time domain of each of said processed electrical signals and said baseline electrical signals.

17. An implantable medication infusion pump as defined in claim 11, wherein the characteristics of said processed electrical signals and said baseline electrical signals related to their relative amplitudes comprise:
the average voltage in the time domain of each of said processed electrical signals and said baseline electrical signals.

18. An implantable medication infusion pump as defined in claim 11, wherein the characteristics of said processed electrical signals and said baseline electrical signals related to their relative amplitudes comprise:
the RMS average voltage in the time domain of each of said processed electrical signals and said baseline electrical signals.

19. An implantable medication infusion pump as defined in claim 11, wherein the characteristics of said processed electrical signals and said baseline electrical signals related to their relative amplitudes comprise:
the integral in the time domain of each of said processed electrical signals and said baseline electrical signals.

20. An implantable medication infusion pump as defined in claim 11, wherein the characteristics of said processed electrical signals and said baseline electrical signals related to their relative amplitudes comprise:
the peak level in the frequency domain of each of said processed electrical signals and said baseline electrical signals.

21. An implantable medication infusion pump as defined in claim 11, wherein the characteristics of said processed electrical signals and said baseline electrical signals related to their relative amplitudes comprise:
the level at a particular frequency in the frequency domain of each of said processed electrical signals and said baseline electrical signals.

22. An implantable medication infusion pump as defined in claim 21, wherein said particular frequency is approximately 1200 Hz to 1700 Hz.

23. A method as defined in claim 11, wherein the characteristics of said processed electrical signals and said baseline electrical signals related to their relative amplitudes comprise:

the average level in the frequency domain of each of said processed electrical signals and said baseline electrical signals.

24. A method as defined in claim 11, wherein the characteristics of said processed electrical signals and said baseline electrical signals related to their relative amplitudes comprise:
the RMS average level in the frequency domain of each of said processed electrical signals and said baseline electrical signals.

25. A method as defined in claim 11, wherein the characteristics of said processed electrical signals and said baseline electrical signals related to their relative amplitudes comprise:
the integral in the frequency domain of each of said processed electrical signals and said baseline electrical signals.

26. An implantable medication infusion pump as defined in claim 1, wherein said logic means utilizes characteristics related to the slop of the relative amplitudes of said filtered electrical signals during repetitive, closely spaced pumping cycles to determine an operational condition of the implanted medication infusion pump relating to fluid not being properly pumped.

27. An implantable medication infusion pump as defined in claim 26, wherein said logic means indicates a partially encapsulated or occluded catheter when repeated downward slope patterns are present.

28. An implantable medication infusion pump as defined in claim 1, wherein said informational signal comprises:
a low level "tickle" electrical signal.

29. An implantable medication infusion pump as defined in claim 1, wherein said informational signal comprises:
an audible signal.

30. An implantable medication infusion pump as defined in claim 1, wherein said implantable medication infusion pump comprises means for providing telemetered information to an external receiver, and wherein said informational signal comprises:
a telemetered signal indicative of the existence of a system malfunction.

31. An implantable medication infusion pump as defined in claim 1, additionally comprising:
means for inhibiting the operation of said transferring means if said logic means determines the existence of a system malfunction.

32. An implantable medication infusion pump including apparatus for diagnosing a system malfunction, comprising:
a reservoir for containing a fluid medication;
means for transferring said fluid medication from said reservoir to a location outside said implantable medication infusion pump;
means located in said implantable medication infusion pump adjacent to said transferring means for generating electrical signals proportional to acoustic signals generated by said transferring means;
means for filtering said electrical signals to produce filtered electrical signals;
means for determining a characteristic related to the relative amplitude of said filtered electrical signals;
means for comparing said characteristic related tot he relative amplitude of said filtered electrical signals to a characteristic of baseline electrical signals related to their relative amplitude to determine an operational condition of the implanted medication infusion pump relating to fluid not being properly pumped, said comparing means providing a first informational signal if said filtered electrical signals are greater than or equal to a first predetermined value, said comparing means providing a second informational signal if said filtered electrical signals are smaller than or equal to a second predetermined value, said second predetermined value being smaller than said first predetermined value; and
means for providing an information signal if said logic means determines the existence of a system malfunction.

33. An implantable medication infusion pump including apparatus for diagnosing a system malfunction, comprising:
a reservoir for containing a fluid medication;
means for transferring said fluid medication from said reservoir to a location outside said implantable medication infusion pump;
means located in said implantable medication infusion pump adjacent to said transferring means for generating electrical signals proportional to acoustic signals generated by said transferring means;
means for filtering said electrical signals to produce filtered electrical signals;
logic means for utilizing a characteristic related to the slope of the relative amplitudes of said filtered electrical signals during repetitive, closely spaced pumping cycles to determine an operational condition of the implanted medication infusion pump relating to fluid not being properly pumped, said logic means providing a first informational signal if said slope is greater than or equal to a first predetermined value, said logic means providing a second informational signal if said slope is smaller than or equal to a second predetermined value, said second predetermined value being smaller than said first predetermined value; and
means for providing an informational signal if said logic means determines the existence of a system malfunction.

34. An implantable medication infusion pump including apparatus for diagnosing a system malfunction, comprising:
a reservoir for containing a fluid medication;
means for transferring said fluid medication from said reservoir to a location outside said implantable medication infusion pump;
means located in said implantable medication infusion pump adjacent to said transferring means for generating electrical signals proportional to acoustic signals generated by said transferring means;
logic means for utilizing a characteristic related to the relative amplitude of said electrical signals to determine an operational condition of the implanted medication infusion pump relating to fluid not being properly pumped, said logic means providing a first informational signal if said amplitude of said electrical signals are greater than or equal to a first predetermined value, said logic means providing a second informational signal if said amplitude of said electrical signals are smaller than or equal to a second predetermined value, said second predetermined value being smaller than said first predetermined value.

35. A method of diagnosing a system malfunction in an implantable medication infusion pump containing a reservoir for containing a fluid medication, and a mechanism for transferring said fluid medication from said reservoir to a location outside said implantable medication infusion pump, said method comprising:

generating electrical signals proportional to acoustic signals generated by the transferring mechanism with a transducer located in said implantable medication infusion pump adjacent to said mechanism for transferring said fluid medication;

filtering said electrical signals to produce filtered electrical signals;

utilizing a characteristic related to the relative amplitude of said filtered electrical signals to determine an operational condition of the implanted medication infusion pump relating to fluid not being properly pumped;

providing a first informational signal if said filtered electrical signals are greater than or equal to a first predetermined value, indicating the existence of a first type of system malfunction; and providing a second information signal if said filtered electrical signals are less than or equal to a second predetermined value, indicating the existence of a second type of system malfunction.

* * * * *